United States Patent [19]
Overtoom

[11] Patent Number: 6,066,113
[45] Date of Patent: May 23, 2000

[54] SYSTEM FOR TREATING THE URETER AND/OR PYELO-URETER JUNCTION

[76] Inventor: Timotheus Theodorus Cornelis Overtoom, Gezichtslaan 1a, NL-3723 Ga Bilthoven, Netherlands

[21] Appl. No.: 09/066,430
[22] PCT Filed: Nov. 1, 1996
[86] PCT No.: PCT/NL96/00432
§ 371 Date: Sep. 16, 1998
§ 102(e) Date: Sep. 16, 1998
[87] PCT Pub. No.: WO97/16218
PCT Pub. Date: May 9, 1997

[30] Foreign Application Priority Data

Nov. 2, 1995 [NL] Netherlands ............... 1001564

[51] Int. Cl.[7] ........................... A61M 25/10
[52] U.S. Cl. .............................. 604/96; 604/8
[58] Field of Search ............... 606/192, 194; 604/96, 8

[56] References Cited

U.S. PATENT DOCUMENTS

| | | | |
|---|---|---|---|
| 4,155,364 | 5/1979 | Boxer | 128/349 B |
| 4,571,239 | 2/1986 | Heyman | 604/54 |
| 4,575,371 | 3/1986 | Nordqvist et al. | 604/96 |
| 5,002,558 | 3/1991 | Klein et al. | 606/192 |
| 5,024,655 | 6/1991 | Freeman et al. | 604/96 X |
| 5,312,430 | 5/1994 | Rosenbluth et al. | 606/192 |
| 5,318,529 | 6/1994 | Kontos | 604/96 |

FOREIGN PATENT DOCUMENTS

| | | |
|---|---|---|
| 0552934 | 7/1993 | European Pat. Off. . |
| 8203557 | 10/1982 | WIPO . |

*Primary Examiner*—Michael H. Thaler
*Attorney, Agent, or Firm*—Webb Ziesenheim Logsdon Orkin & Hanson, P.C.

[57] ABSTRACT

The invention relates to a system for treating the ureter and/or the pyelo-ureter junction, comprising: a widener for widening a constriction, a guide for guiding the widener through the urethra, bladder and ureter, wherein the guide is introducible into the patient through the urethra, bladder and ureter to extend beyond pyelo-ureter junction, whereafter the widener is introducible along the guide and is subsequently able to be widened in order to widen the constriction whereafter the widener is removable.

19 Claims, 11 Drawing Sheets

SYSTEM FOR TREATING THE URETER AND/OR PYELO-URETER JUNCTION

The present invention relates to a system of apparatus for treating the ureter and/or the pyelo-ureter junction.

Blockages in the ureter which are generally caused by constriction thereof (in medical terms: a stenosis) can lead to serious medical problems such as pain, inflammation of the ureter wall and prevention of urine drainage from the kidney.

A constriction in the pyelo-ureter junction or more distally in the ureter was until recently treated by means of an operation termed pyeloplasty or ureterdlasty. This meant that the kidney is exposed following a rather large incision in the flank whereafter the pyelum is surgically corrected.

This operation has recently been replaced by an endoscopic method wherein a nefrostomy catheter is placed into the surgically expanded pyelum. Under nefrostomy it is to be understood: arranging an alternative deviation for urine drainage by means of a catheter which is placed into the pyelum via the back, or rather the kidney, this being carried out in the X-ray department and usually not done under general anaesthetic. In spite of local anaesthetic, this operation can however be very painful. A pyeloscopy is subsequently carried out, wherein the pyelum is treated with a scope, which can be introduced in one or two ways:

1) via the ureter bladder and ureter into the pyelum, wherein the scope is a flexible fibre glass scope. This operation is usually impossible when the ureter is constricted.
2) through a tube (10–15 mm in diameter) which is introduced through the back into the pyelum after the above mentioned nefrostomy has been carried out.

This second operation is carried out under general anaesthetic in the operating theatre.

By these known treatments, a guide wire is manipulated through the constriction from the pyelum through the bladder with the aid of the scope, over which guide wire a PTA balloon is pushed.

A PTA balloon, or rather a "percutaneous transluminal angioplasty balloon" is a catheter balloon which is commonly used to widen blood vessel constrictions, and introduced by means of a guide wire which has been pushed into the blood vessel wall. Depending on the balloon diameter, this can resist a maximum pressure of between 4 to ±17 atm.

This balloon is expanded to a pressure of 10–17 atmospheres in order to stretch and widen the ureter wall at the position of the stenosis.

The balloon is subsequently removed. Whilst the guide wire remains, the constriction is further widened in the longitudinal direction by one or more surgical incisions.

An endopyelotomy stent is then pushed over the wire and into the bladder. This is a catheter having a curled end situated in the pyelum, whereby the other end is curled in the bladder in order not to project into the bladder wall. This stent functions to keep open the constriction in order to prevent a relapse.

This catheter has a maximum diameter of 4.7 mm and cannot be introduced into the ureter from the bladder due to the constriction. After a period of roughly six weeks, the catheter can be pulled out of the ureter from the bladder. During this period, the ureter has had time enough to heal around this catheter and to widen. Through a channel in the catheter, urine drainage is carried out during these six weeks.

An object of the present invention is to provide a system wherein treatment of the ureter and/or the pyelo-ureter junction is less stressful for the patient.

SUMMARY OF THE INVENTION

There is provided according to the present invention a system for treating the ureter and/or the pyelo-ureter junction.

Since the widening means which preferably comprise a first balloon, are introduced via a guiding means from the bladder, admission of a patient into a hospital, whereby nefrostomy as well as endopyelotomy. under general anaesthetic and the accompanying uncomfortable and costly circumstances are required, is avoided.

The system preferably further comprises keeping open means in order to keep open the now widened constriction, wherein the keeping open means preferably comprise a second balloon.

The inventor has found that a constriction such as in the pyelo-ureter junction can be expanded under high pressure, and kept in this expanded, widened state at a lower pressure, in which state healing occurs.

In order to drain urine, the system can comprise a urine drainage catheter.

The diameter of the first expandable balloon is preferably larger than the diameter of the bottom end of the second expandable balloon, at the position of the constriction, in order to prevent that the second balloon is placed too tightly against the constriction.

The diameter of the first balloon is preferably smaller than the broadest part of the second balloon which lies closer to the pyelum, in order to prevent that the latter slips below the constriction and into the ureter.

Since the measurements of the system according to the present invention are mainly dependent on the patient, the following table gives an indication of exemplary maxima and minima for the expanded upper end and bottom end for the second balloon.

|  | Upper end diameter (mm) | Bottom end diameter (mm) |
| --- | --- | --- |
| Adults | 14 | 7 |
| ↑ | 12 | 6 |
| ↓ | 10 | 5 |
| Children | 8 | 4 |

A single balloon expandable under different pressures to yield the various desired upper and bottom end diameters is also conceivable according to the present invention.

BRIEF DESCRIPTION OF THE DRAWINGS

Further advantages and aspects of the present invention are to be found in the claims and are clarified with respect to FIGS. 1–8 wherein a stedwise treatment of the ureter and the pyelo-ureter junction with the system according to the present invention is shown. In the above table and in FIGS. 9 to 13, the expansion and deflation of the balloon catheter making up part of the system according to the present invention via an assembly is stepwise illustrated.

DETAILED DESCRIPTION OF THE PREFERRED EMBODIMENTS

Figure 1:
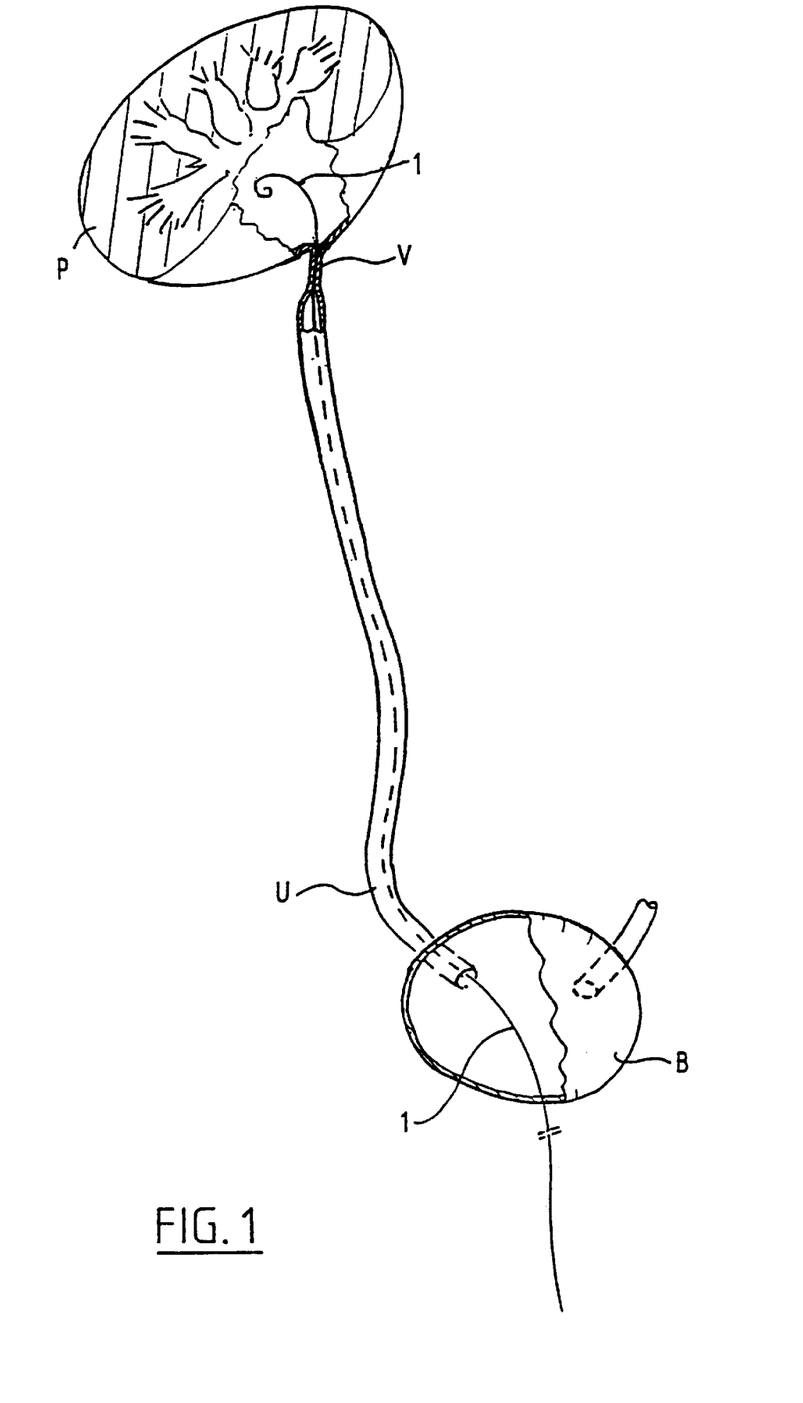
Figure 2:
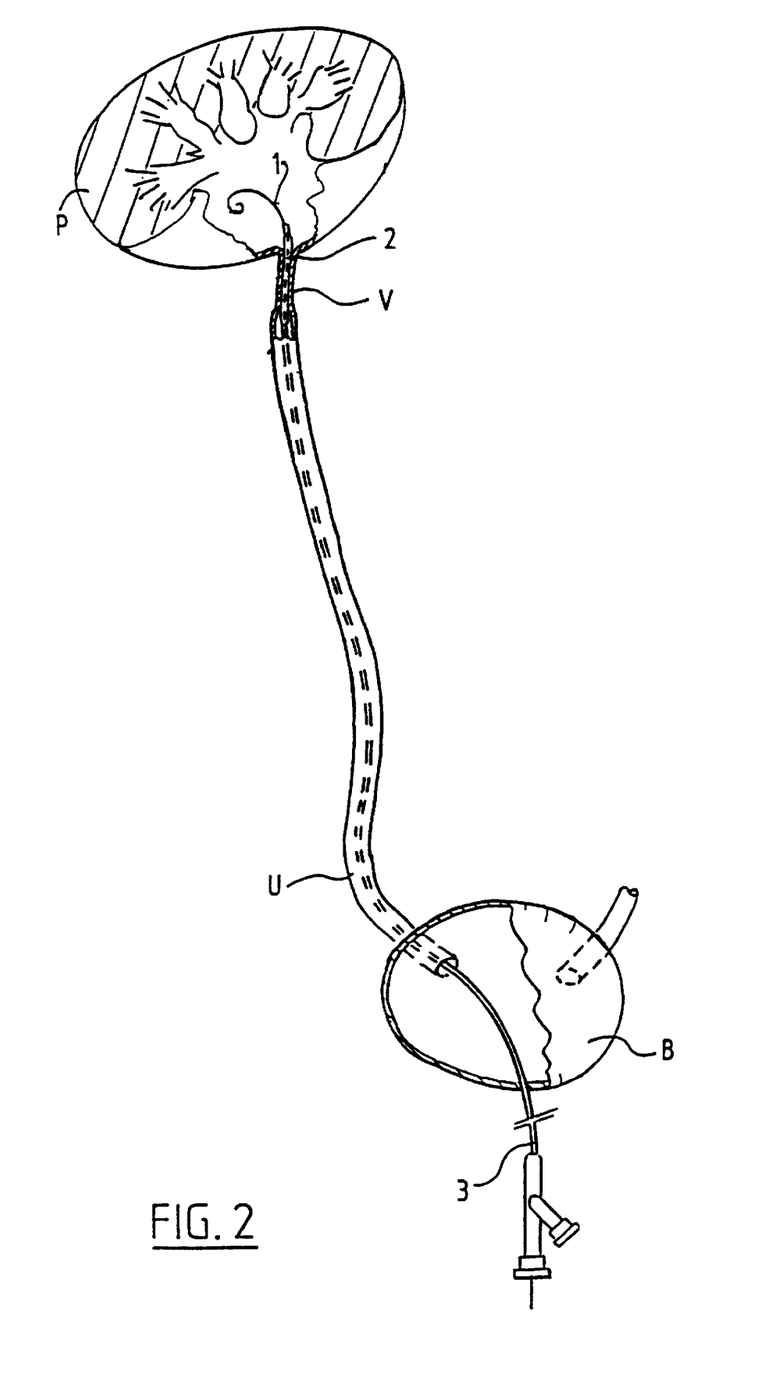
Figure 3:
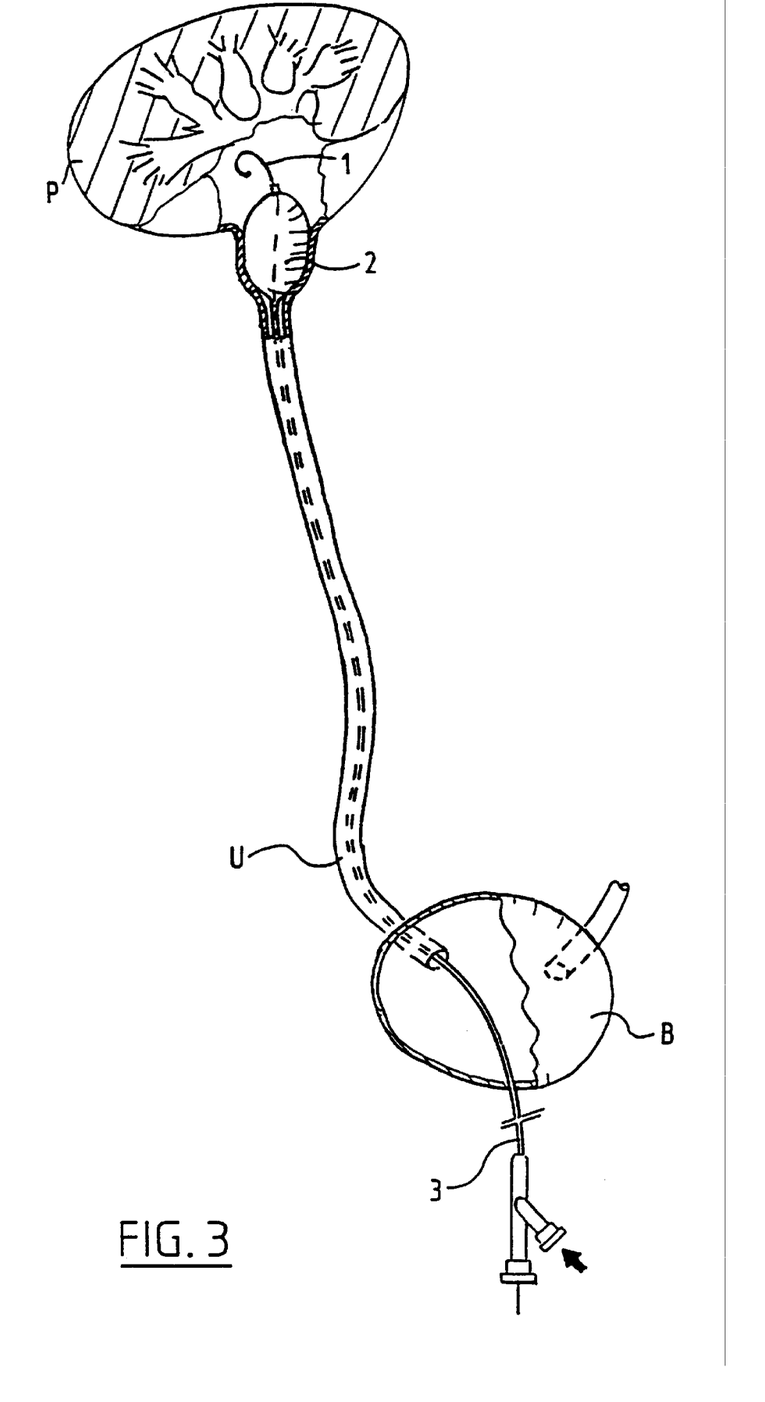
Figure 4:
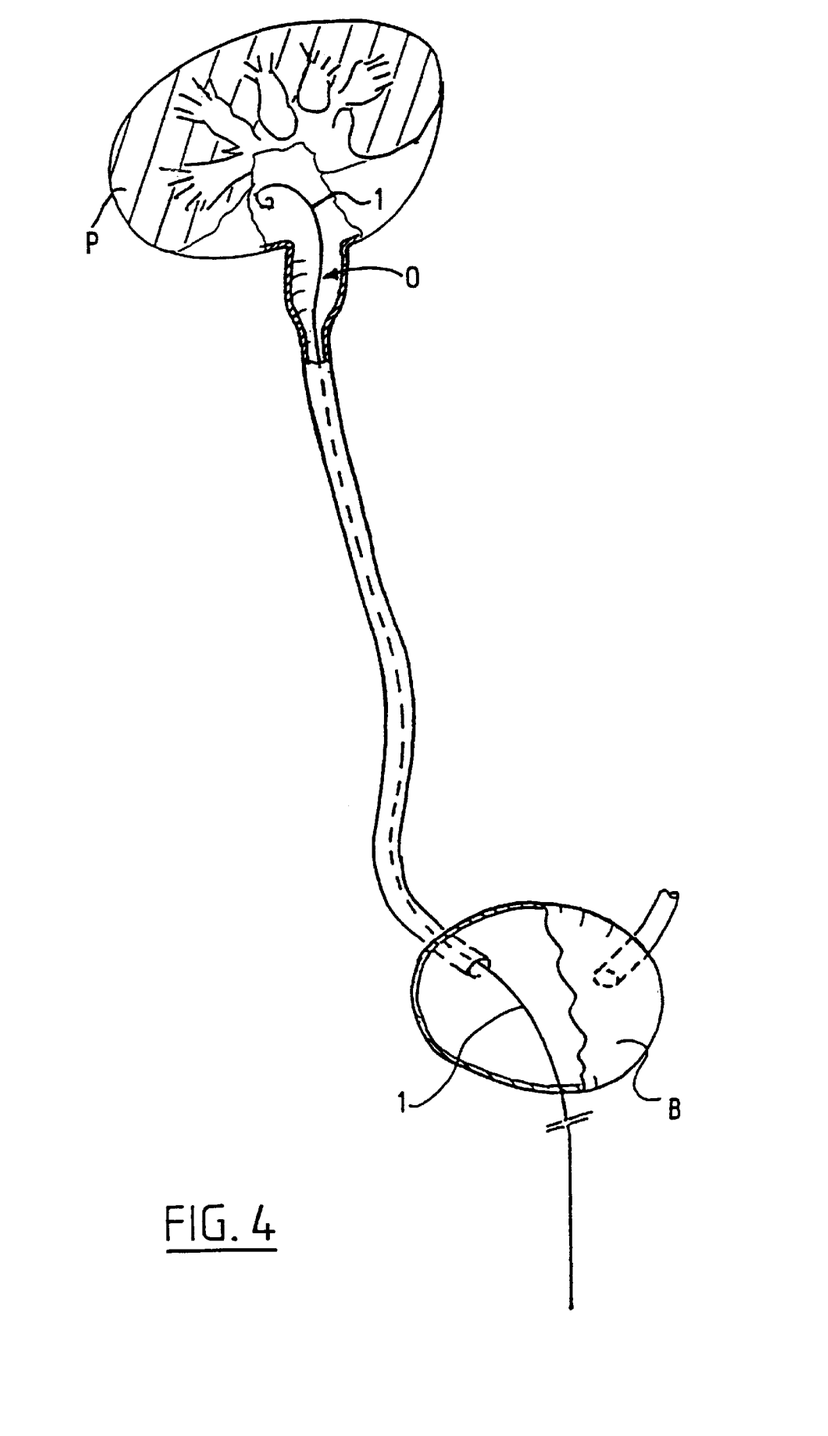
Figure 5:
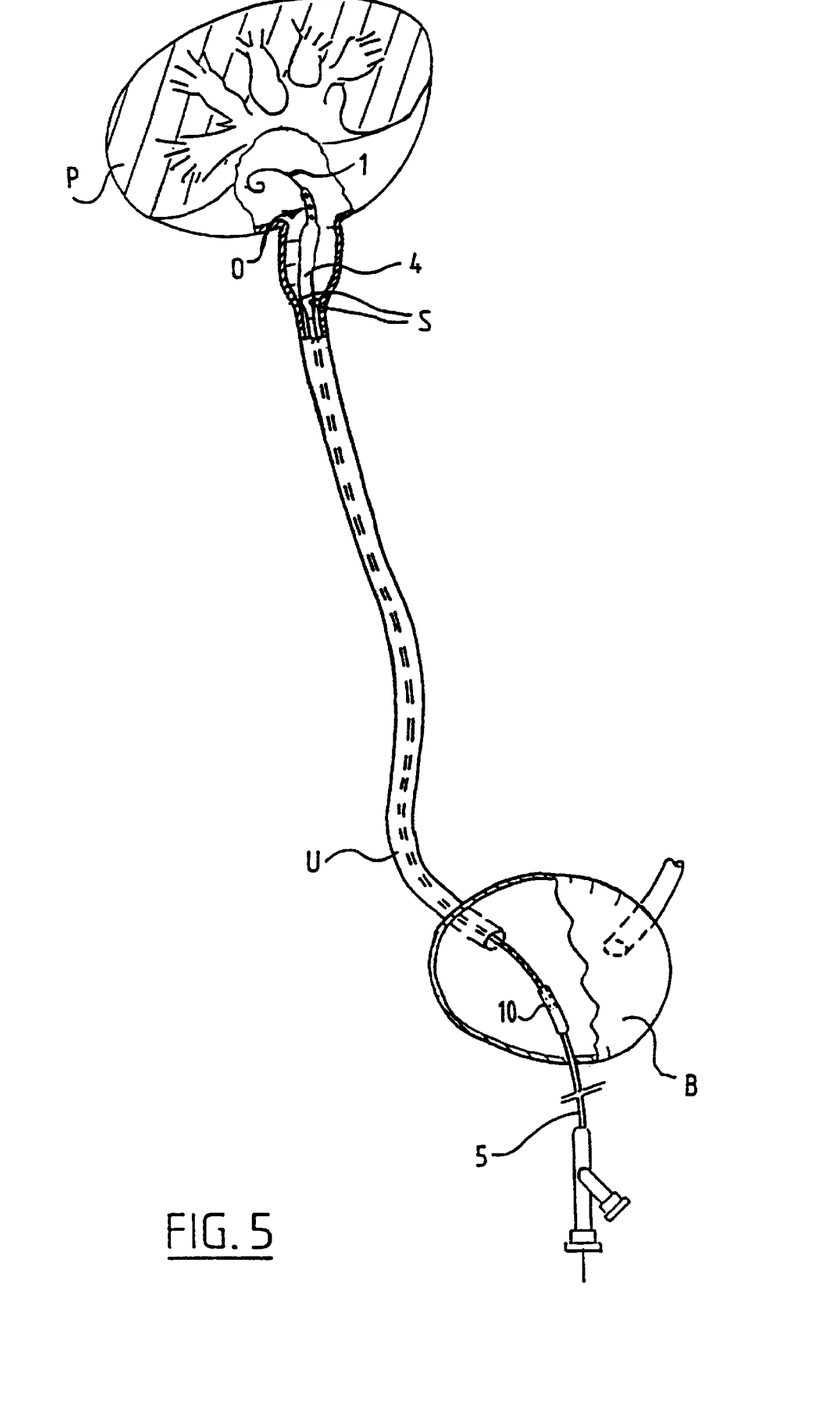

Firstly, guiding means in the form of a wire element 1 (FIGS. 1–7) are introduced via the urethra (not shown), the bladder (B) and the ureter (U) to extend beyond the constriction (V) (FIG. 1). Since an increased pressure exists in the pyelum due to the constriction, the pyelum has a pumped up, exdanded form. A percutaneous angioplasty balloon 2 is pushed over the wire element 1 to past the constriction (V) (FIG. 2). This balloon 2 is subsequently expanded under a high pressure of roughly 17 atmospheres during one to two minutes for example, whereby the constriction is widened (see FIG. 3). This expansion time can in certain situations be longer according to desires, e.g. for up to 10 minutes to prevent bleeding, i.e. to allow time for the congealing of blood from possible wounds. Thereafter, the balloon 2 is allowed to deflate and is removed by pulling this back over the wire element 1 through the ureter (U), bladder (B) and urethra and thus out of the patient. The inventor has had the insight that the pyelo-ureter junction (O) remains in this widened state (FIG. 4), for a period of time.

Figure 6:
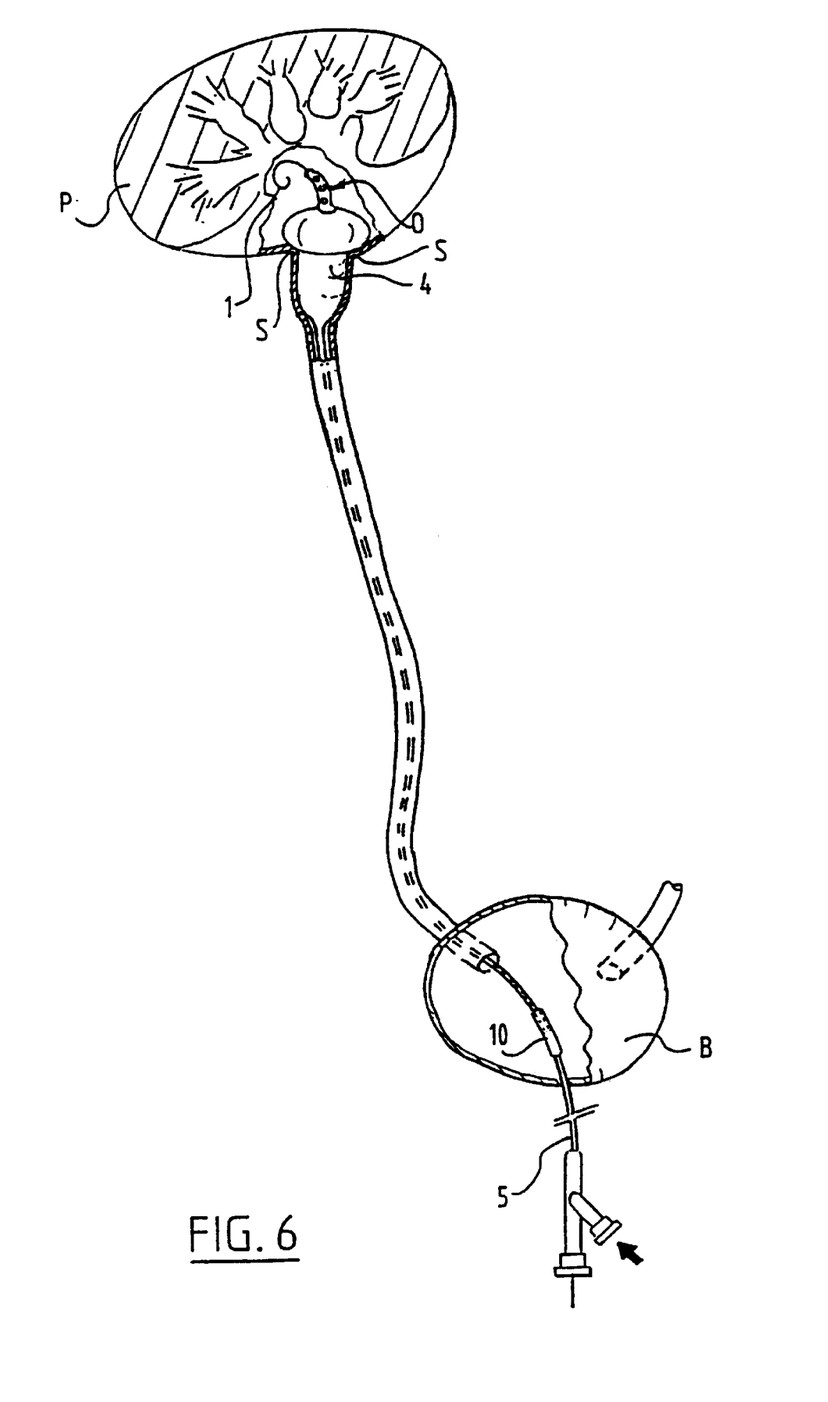
Figure 7:
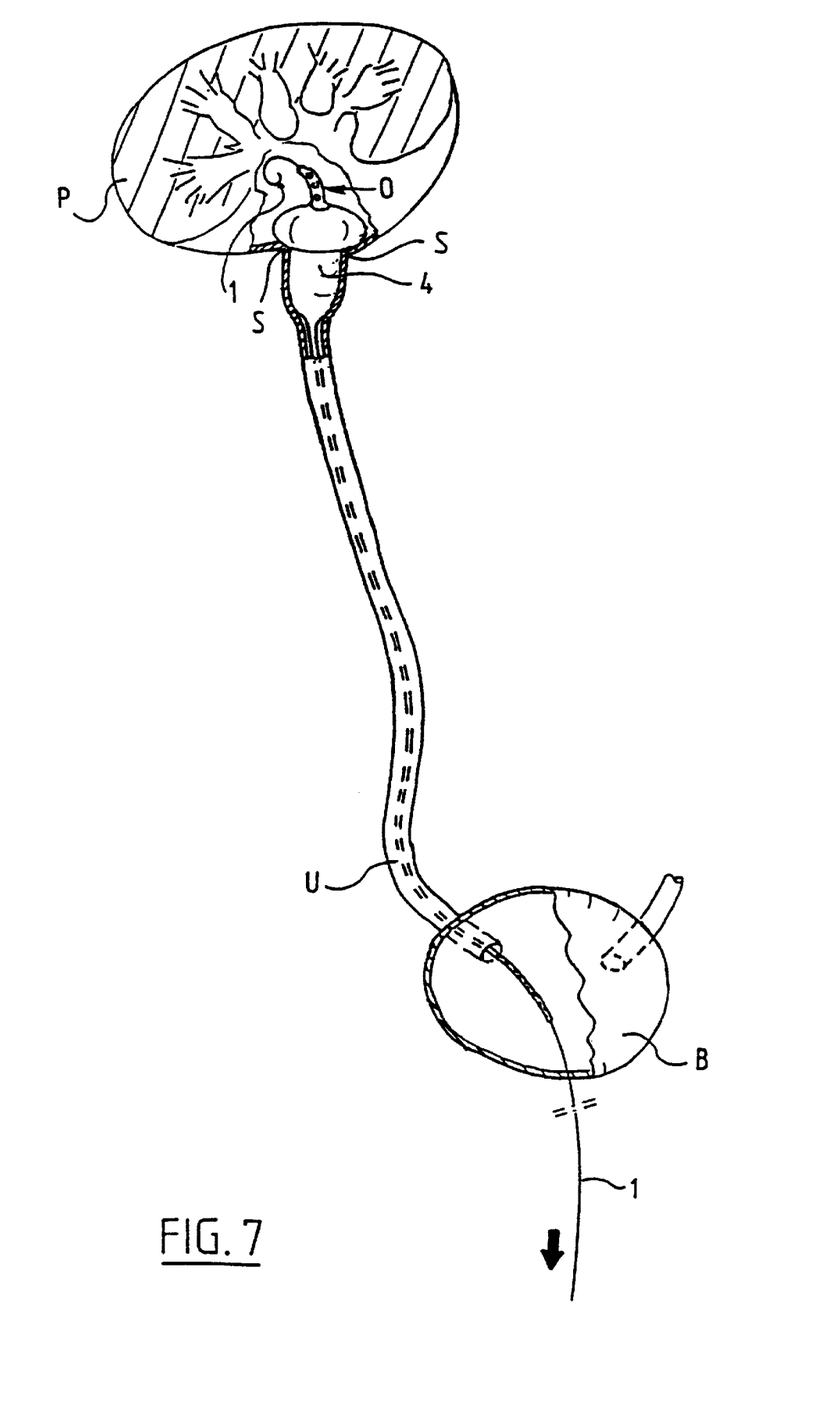

Subsequently, a balloon catheter 4 is arranged in the pyelum (P) with the aid of an introducing or pushing catheter 5 (FIG. 5) which introduces said balloon catheter 4 over the wire element 1 through the urethra, bladder (B) and ureter (U) into the pyelum (P) When the balloon catheter 4 is arranged at the desired position, it is expanded in order to keep open the pyelo-ureter junction (O). Since the balloon catheter 4 has a greater expandable diameter at the pyelum side than the ureter side, this can derend from the "shoulders" (S) of the pyelum-ureter junction (O), whereby the RUPP-balloon catheter 4 does not drop into the ureter (U) (FIG. 6).

Since the balloon catheter 4 keeps the pyelo-ureter (O) open without exerting a high pressure thereon, preferably a pressure of 6 atmospheres and minimally 4 atmospheres, healing of the pyelo-ureter junction (O) can take place in an optimum manner.

After inflation of the balloon catheter 4, the pushing catheter 5 is decoupled and removed, preferably via the assembly 10 (see FIGS. 9–13 and FIGS. 5 and 6), whereby the balloon catheter 4 remains behind in its expanded form and does not deflate.

Figure 8:
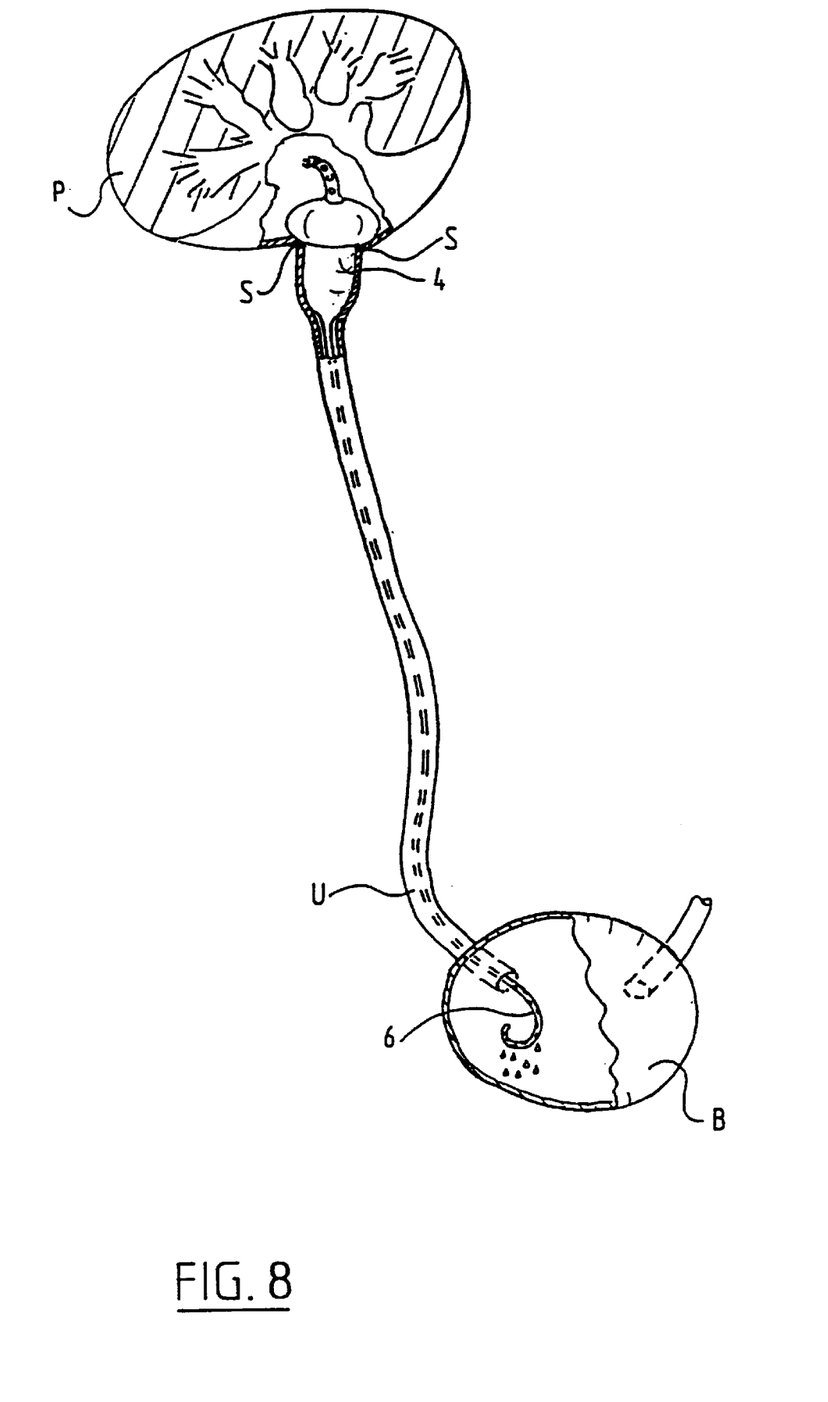

The wire element 1 is subsequently removed (FIG. 7), wherein the end of the balloon catheter 4 situated in the bladder (B) curls up in the bladder (B) (FIG. 8).

During the period that the balloon catheter 4 remains in place, both ends thereof which are situated respectively in the pyelum and the bladder, as well as the perforations in the balloon tail 6, take care of the urine discharge.

After about six weeks, this end of the balloon catheter 4 is severed, whereafter the balloon catheter 4 deflates and can be removed through the ureter, bladder and urethra.

The assembly 10 comprises a tube section 12 of the balloon catheter 4 having a balloon inflation fluid contrast medium channel 14 and a catheter channel 16.

The tube section 12 is removably joined with a pipe element 18 also having an inflation fluid channel 20 and a catheter channel 21, (FIG. 9) which correspond with the channels 14 and 16 respectively of the tube section 12 of the balloon catheter 4.

An opening 24 is associated in the tube section 12 extending between the fluid channel 14 and the exterior. This opening, as shown in FIGS. 9–12, is closed off by a slidable closing ring 26 arranged around the tube section 12 of the balloon catheter 4 in a recess 28 thereof. A silicon plug 30 is situated in the fluid channel 14, which plug preferably has a conical shape to ensure an optimum air tightness.

A hollow needle 32, associated with the pipe element fluid channel 20 extends through the silicon plug 30, when introducing fluid into the fluid channel 14.

Figure 9:
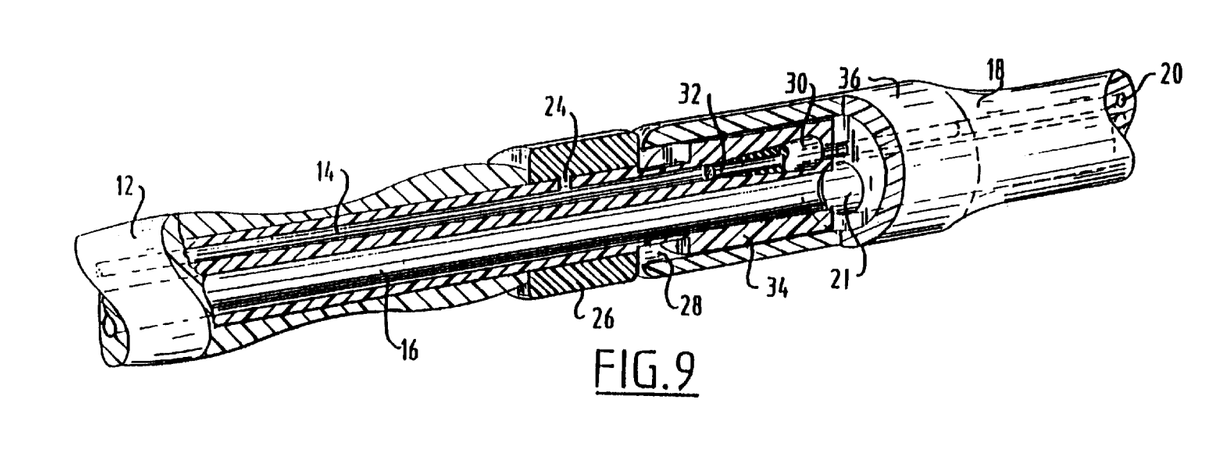
Figure 10:
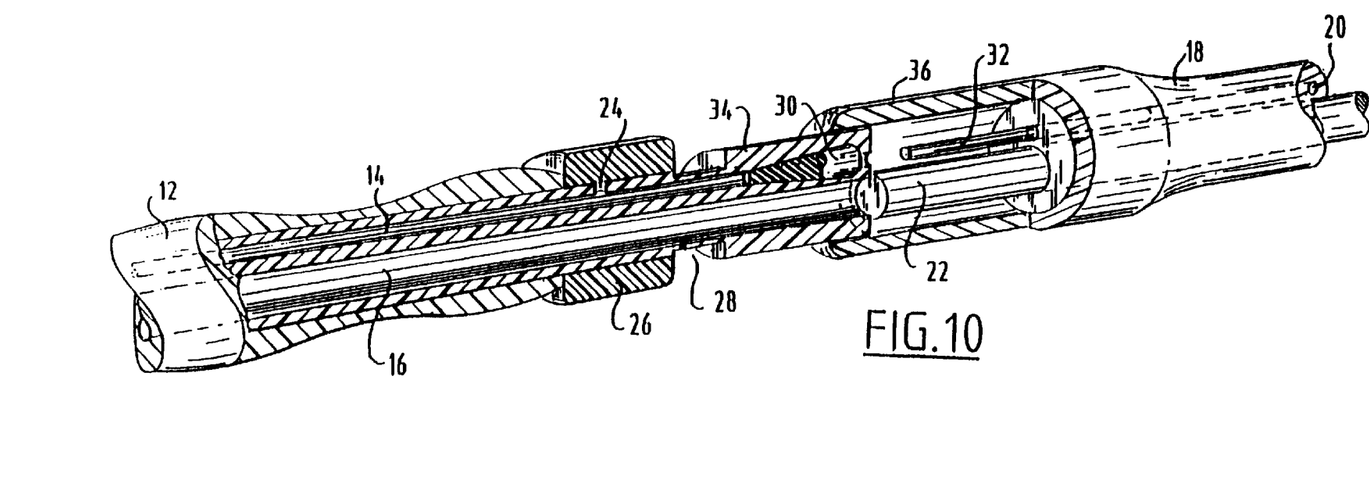
Figure 11:
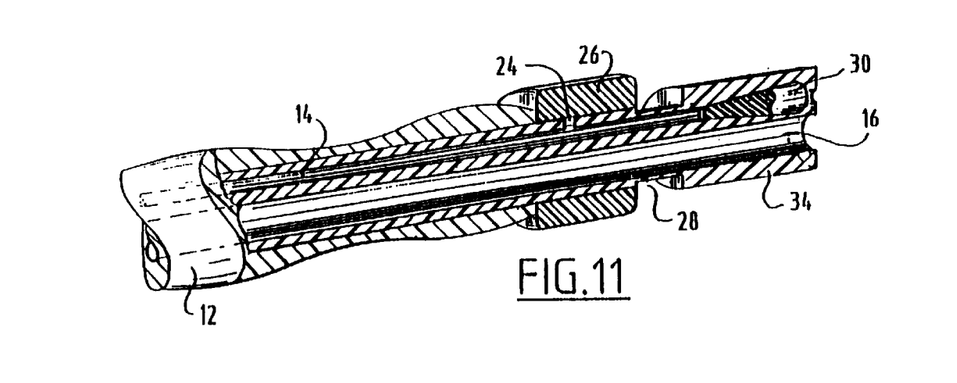
Figure 12:
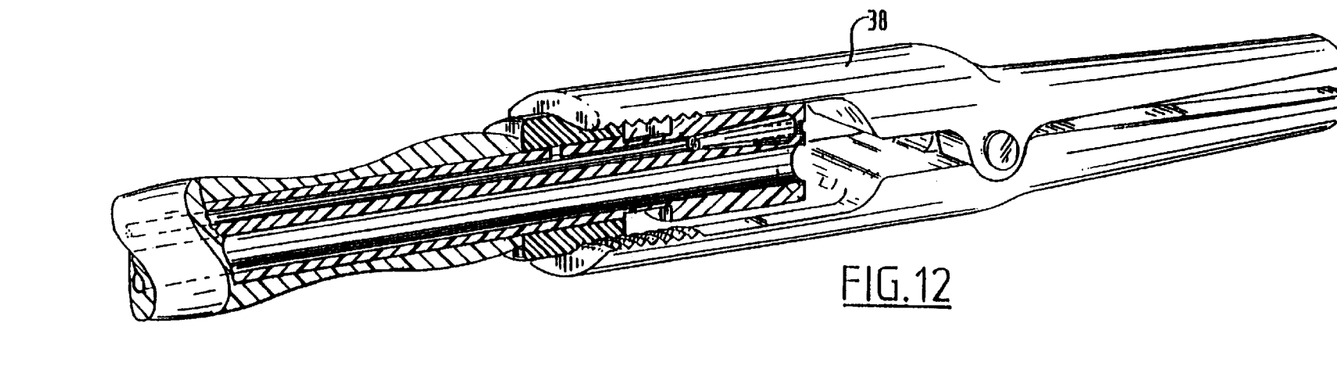
Figure 13:
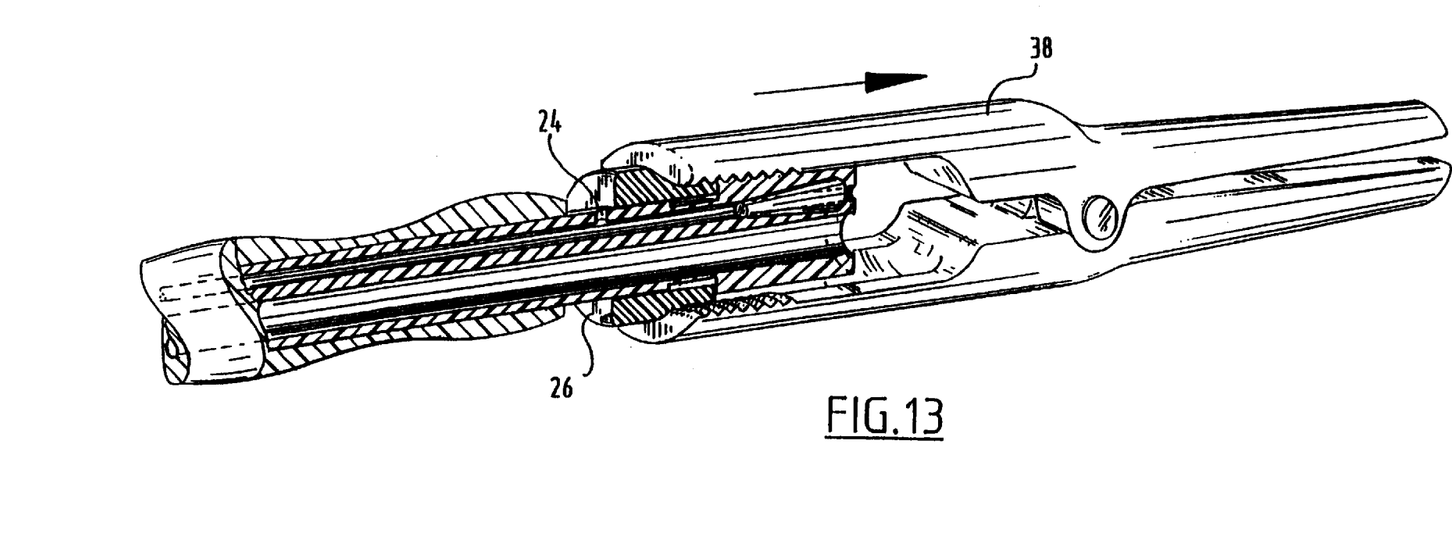

In use, the balloon catheter 4 is inserted into the patient as here above described, whereaf ter the pipe element 18 is pushed over a distal end 34 of the tube section 12 of the balloon catheter 4, so that a flared end section 36 of the pipe element 18 passes over the distal section 34 of the tube section 12 until it comes to rest against the closing ring 26. On pushing further of the piDe element 18, the closing ring 26 is pushed over the opening 24 and the needle 32 is pushed through the silicon plug 30. At this point the pipe element fluid channel 20 and the balloon fluid channel 14 correspond with each other (FIG. 9).

Fluid can then be introduced into the balloon fluid channel 14, via the pipe element fluid channel 20, through the hollow needle 32, whereby the balloon catheter 4 is inflated.

Following inflation of the balloon 4 (see FIGS. 5 and 6), the pipe element 18 is decoupled from the tube section 12 by pushing a flexible iron rod 22 (FIG. 10) through the channel 21 (FIG. 9) of the pipe element 18. Channel 21 of the pipe element 18 corresponds with the catheter channel 16 of the tube section 12, but is broader in diameter. On pushing the flexible rod 22 through the channel 21, the former comes to push against the distal end 34 of the tube section 12, whereby the distal end 34 is pushed free from the flared end section 36 of the pide element 18. The needle 32 is also simultaneously removed from the plug 30 by this action.

Since the tube section 12 is pushed free from the pipe element 18, problems which could arise by pulling the pipe element free, whereby the balloon catheter could also be pulled out of position are avoided.

In this way, a detachable retrograde ureter pyeloplasty balloon, which can be decoudled and left inflated at the pyelo-ureter junction is provided. on having been decoupled (see FIG. 11), the fluid channel 14 remains closed off by the closing ring 26, whereby the catheter balloon 4 remains inflated at the pyelo-ureter junction for the desired period of time.

In order to remove the balloon catheter 4, the surgeon or urologist, with the aid of a gripping tool 38 (FIG. 12) merely slides the displaceable closing ring 26 over the recess 28 towards the distal end 34 of the tube section 12, thereby exposing the opening 24 (FIG. 13) wherethrough the inflation fluid can escape which leads to deflation of the balloon catheter 4.

Following deflation, the balloon catheter can then be simply removed, via the ureter, bladder and urethra.

I claim:

1. A system for treating the ureter and/or the pyelo-ureter junction, comprising:

widening means for widening a constriction in the ureter and/or the pyelo-ureter junction, the widening means including a first inflatable balloon;

an expandable balloon catheter adapted to replace the first inflatable balloon after the constriction is widened, the balloon catheter defining an inflation lumen and a urine drainage lumen, the balloon catheter expandable via the inflation lumen to maintain open in its expanded state the widened constriction; and introducing means including an introducing catheter defining lumens configured to mate with the inflation lumen and the urine drainage lumen of the balloon catheter, and further having a coupling/decoupling means for coupling the lumens to the inflation lumen and the urine drainage lumen such that the introducing catheter is decoupleable from the balloon catheter while the balloon catheter remains substantially inflated.

2. The system according to claim 1, wherein the balloon catheter has a greater expandable diameter at a first extremity thereof, than at a second extremity thereof.

3. The system according to claim 2, wherein the first inflatable balloon has a greater expandable diameter than the second extremity of the balloon catheter.

4. The system according to claim 3, wherein the expanded diameter of the first inflatable balloon is smaller than the expanded diameter of the first extremity of the balloon catheter.

5. The system according to claim 4, wherein the first inflatable balloon can resist a pressure of between 4 and 17 atmospheres.

6. The system according to claim 5, wherein the first inflatable balloon can resist a higher pressure than the balloon catheter.

7. The system according to claim 1, further comprising guiding means which includes at least one wire element for guiding the widening means, the balloon catheter and the introducing means through the urethra, bladder and ureter of a patient.

8. The system according to claim 1, wherein the coupling/decoupling means includes a coupling/uncoupling assembly for an inflation medium introducing element for introducing balloon inflation medium into the balloon catheter, the assembly comprising:

a tube section defining a catheter channel connected to the balloon catheter, and wherein the inflation medium is introducible to the balloon catheter through the catheter channel;

plugging means associated with the catheter channel for plugging the catheter channel;

an opening defined in the tube section and connected to the catheter channel, the opening located between the balloon catheter and the plugging means and through which the inflation medium is escapable from the balloon catheter; and displaceable closing means for closing the opening, wherein the balloon catheter is inflatable by introducing the inflation medium through the catheter channel via an expansion medium introducing element, and wherein the element is detachable from the balloon catheter such that the balloon catheter remains substantially inflated with the inflation medium.

9. The system according to claim 8, wherein the inflation medium introducing element includes a fluid pipe element having a flared end for coupleably engaging the balloon catheter.

10. The system according to claim 9, wherein the fluid pipe element further comprises a hollow needle extendable through the plugging means.

11. The system according to claim 9, wherein the fluid pipe element comprises a flexible pushing member for pushing the balloon catheter free therefrom.

12. A system for treating the ureter and/or the pyelo-ureter junction, comprising:

widening means for widening a constriction in the ureter and/or the pyelo-ureter junction, the widening means including a first inflatable balloon;

an expandable balloon catheter adapted to replace the first inflatable balloon after the constriction is widened, the balloon catheter defining an inflation lumen and a urine drainage lumen, the balloon catheter expandable via the inflation lumen to maintain open in its expanded state the widened constriction;

introducing means including an introducing catheter defining lumens configured to mate with the inflation lumen and the urine drainage lumen of the balloon catheter, and further having coupling/decoupling means for coupling the lumens to the inflation lumen and the urine drainage lumen such that the introducing catheter is decoupleable from the balloon catheter while the balloon catheter remains substantially inflated; and guiding means which includes at least one wire element for guiding the widening means, the balloon catheter and the introducing means through the urethra, bladder and ureter of a patient, wherein the balloon catheter has a greater expandable diameter at a first extremity thereof than at a second extremity thereof.

13. The system according to claim 12, wherein the first inflatable balloon has a greater expandable diameter than the second extremity of the balloon catheter.

14. The system according to claim 13, wherein the expanded diameter of the first inflatable balloon is smaller than the expanded diameter of the first extremity of the balloon catheter.

15. The system according to claim 14, wherein the first inflatable balloon can resist a pressure of between 4 and 17 atmospheres.

16. The system according to claim 15, wherein the first inflatable balloon can resist a higher pressure than the balloon catheter.

17. The system according to claim 12, wherein the coupling/decoupling means includes a coupling/uncoupling assembly for an inflation medium introducing element for introducing balloon inflation medium into the balloon catheter, the assembly comprising:

a tube section defining a catheter channel connected to the balloon catheter, and wherein the inflation medium is introducible to the balloon catheter through the catheter channel;

plugging means associated with the catheter channel for plugging the catheter channel;

an opening defined in the tube section and connected to the catheter channel, the opening located between the balloon catheter and the plugging means and through which the inflation medium is escapable from the balloon catheter; and displaceable closing means for closing the opening, wherein the balloon catheter is inflatable by introducing the inflation medium through the catheter channel via an expansion medium introducing element, and wherein the element is detachable from the balloon catheter such that the balloon catheter remains substantially inflated with the inflation medium.

18. The system according to claim 17, wherein the inflation medium introducing element includes a fluid pipe element having a flared end for coupleably engaging the balloon catheter.

19. The system according to claim 18, wherein the fluid pipe element further comprises a hollow needle extendable through the plugging means.

* * * * *

UNITED STATES PATENT AND TRADEMARK OFFICE
CERTIFICATE OF CORRECTION

PATENT NO. : 6,066,113

DATED : May 23, 2000

INVENTOR(S) : Timothy Theodorus C. OVERTOOM

It is certified that error appears in the above-identified patent and that said Letters Patent is hereby corrected as shown below:

Column 1 Line 1 after the title insert
--BACKGROUND OF THE INVENTION
1. Field of the Invention--.

Column 1 before Line 5 insert --2. Description of the Prior Art--.

Column 1 Line 11 "ureterdlasty" should read --ureterplasty--.

Column 2 Line 4 after "endopyelotomy" delete ".".

Column 2 Line 49 "stedwise" should read --stepwise--.

Column 3 Line 15 after "(P)" insert --.--.

Column 3 Line 64 "whereaf ter" should read --whereafter--.

Column 4 Line 2 "piDe" should read --pipe--.

UNITED STATES PATENT AND TRADEMARK OFFICE
CERTIFICATE OF CORRECTION

PATENT NO. : 6,066,113
DATED : May 23, 2000
INVENTOR(S) : Timothy Theodorus C. OVERTOOM It is certified that error appears in the above-identified patent and that said Letters Patent is hereby corrected as shown below:

Column 4 Line 18 "pide" should read --pipe--.

Column 4 Line 25 "decoudled" should read --decoupled--.

Column 4 Line 26 "provided. on" should read --provided. (new paragraph) On--.

Signed and Sealed this

Twenty-seventh Day of March, 2001

Attest:

NICHOLAS P. GODICI

Attesting Officer

Acting Director of the United States Patent and Trademark Office